(12) United States Patent
Ferguson

(10) Patent No.: US 7,569,795 B2
(45) Date of Patent: *Aug. 4, 2009

(54) HEATER ELEMENT INCORPORATING FUNCTIONAL ELECTRICAL CIRCUIT

(75) Inventor: Patrick Ferguson, North Shields (GB)

(73) Assignee: NEL Technologies Limited, Newcastle Upon Tyne, Tyne & Wear (GB)

( * ) Notice: Subject to any disclaimer, the term of this patent is extended or adjusted under 35 U.S.C. 154(b) by 200 days.

This patent is subject to a terminal disclaimer.

(21) Appl. No.: 11/746,116

(22) Filed: May 9, 2007

(65) Prior Publication Data

US 2007/0210051 A1    Sep. 13, 2007

Related U.S. Application Data

(62) Division of application No. 10/559,024, filed on Apr. 13, 2006, now Pat. No. 7,375,308.

(30) Foreign Application Priority Data

Jun. 2, 2003   (GB) .................................. 0312551.5

(51) Int. Cl.
*H05B 1/00* (2006.01)
*H05B 3/34* (2006.01)

(52) U.S. Cl. ........................ 219/211; 219/549; 219/528; 338/208

(58) Field of Classification Search .................. 219/211, 219/212, 217, 527, 528, 529, 544–549; 392/386, 392/390, 391; 338/208–211, 258, 259, 262, 338/275

See application file for complete search history.

(56) References Cited

U.S. PATENT DOCUMENTS

| 2,717,949 A | 9/1955 | Challenner |
| 3,296,415 A | 1/1967 | Eisler |
| 3,660,088 A | 5/1972 | Lungsager |
| 3,767,398 A | 10/1973 | Morgan |
| 4,201,825 A | 5/1980 | Ebneth |
| 4,257,176 A | 3/1981 | Hartung et al. |

(Continued)

FOREIGN PATENT DOCUMENTS

DE     3210097     9/1983

(Continued)

OTHER PUBLICATIONS

US 6,290,977, 9,2001, Friars et al. (withdrawn).

(Continued)

*Primary Examiner*—Tu B Hoang
*Assistant Examiner*—Vinod D Patel
(74) *Attorney, Agent, or Firm*—Barlow, Josephs & Holmes, Ltd.

(57) ABSTRACT

Disclosed is a breathable heater element for a garment or for the lining of a garment such as an outdoor jacket, e.g. a waterproof jacket. The heater element is formed from porous metallised fabric such a nickel plated woven polyester fabric by photochemical etching of a suitable track pattern onto the metallised fabric. The formed heater element is then laminated into a lining. The material of the lining may be impregnated with microencapsulated functional chemicals such as fragrances, perfumes, antimicrobials or insect repellents. The microcapsules release their contents on activation due to heat generated by the heater element.

20 Claims, 3 Drawing Sheets

U.S. PATENT DOCUMENTS

| | | | |
|---|---|---|---|
| 4,565,745 | A | 1/1986 | Kaminskas |
| 4,743,740 | A | 5/1988 | Adee |
| 4,798,933 | A | 1/1989 | Annovi |
| 4,948,951 | A | 8/1990 | Balzano |
| 5,041,717 | A | 8/1991 | Shay, III et al. |
| 5,352,862 | A | 10/1994 | Barr |
| 5,534,021 | A | 7/1996 | Dvoretzky et al. |
| 5,580,573 | A | 12/1996 | Kydonieus et al. |
| 5,648,003 | A | 7/1997 | Liang et al. |
| 5,829,171 | A | 11/1998 | Weber et al. |
| 6,172,344 | B1 | 1/2001 | Gordon et al. |
| 6,227,458 | B1 | 5/2001 | Dever et al. |
| 6,229,123 | B1 | 5/2001 | Kochman et al. |
| 6,294,313 | B1 | 9/2001 | Kobayashi et al. |
| 6,309,986 | B1 | 10/2001 | Flashinski et al. |
| 6,423,018 | B1 | 7/2002 | Augustine |
| 6,436,063 | B1 | 8/2002 | Augustine et al. |
| 6,501,055 | B2 | 12/2002 | Rock et al. |
| 6,551,560 | B1 | 4/2003 | Flashinski et al. |
| 6,613,350 | B1 | 9/2003 | Zhang et al. |
| 7,115,844 | B2 * | 10/2006 | Ferguson ................ 219/549 |
| 7,375,308 | B2 * | 5/2008 | Ferguson ................ 219/549 |
| 2001/0002669 | A1 | 6/2001 | Kochman et al. |
| 2003/0124167 | A1 | 7/2003 | Thies |
| 2007/0187392 | A1 | 8/2007 | Ferguson |
| 2007/0210051 | A1 | 9/2007 | Ferguson |

FOREIGN PATENT DOCUMENTS

| | | | |
|---|---|---|---|
| GB | 2092868 | * | 8/1982 |
| GB | 2092868 | A | 8/1982 |
| GB | 2175849 | A | 12/1986 |
| GB | 2205496 | A | 12/1988 |
| GB | 2236514 | A | 10/1999 |
| GB | 2336514 | * | 10/1999 |
| GB | 2336514 | A | 10/1999 |
| GB | 2383197 | A | 6/2003 |
| JP | 6147686 | | 3/1986 |
| JP | 03037021 | | 2/1991 |
| JP | 04002079 | | 1/1992 |
| WO | 8810058 | A1 | 12/1988 |
| WO | 0101855 | A1 | 1/2001 |
| WO | 0124580 | | 4/2001 |
| WO | 0124580 | A1 | 5/2001 |
| WO | 03039417 | A2 | 5/2003 |
| WO | 03039417 | | 6/2003 |
| WO | 03053101 | | 6/2003 |
| WO | 2004107818 | A1 | 12/2004 |

OTHER PUBLICATIONS

Adeyeye, C. M. and Price, J. C., "Development and Evaluation of Sustained Release Ibuprofen-Wax Microspheres: I. Effect of Formulation Variables on Physical Characteristics", Pharmaceutical Research, vol. 8, No. 11, pp. 1377-1383 (1991).

Adeyeye, C. M. and Price, J. C., "Development and Evaluation of Sustained Release Ibuprofen-Wax Microspheres: II. In vitro Dissolution Studies", Pharmaceutical Research vol. 11, No. 4, pp. 575-579 (1994).

Adeyeye, C. M. and Price, J. C., "Chemical, dissolution stability and microscopic evaluation of suspensions of ibuprofen-wax microspheres", Journal of Microencapsulation, vol. 14, pp. 357-377 (1997).

* cited by examiner

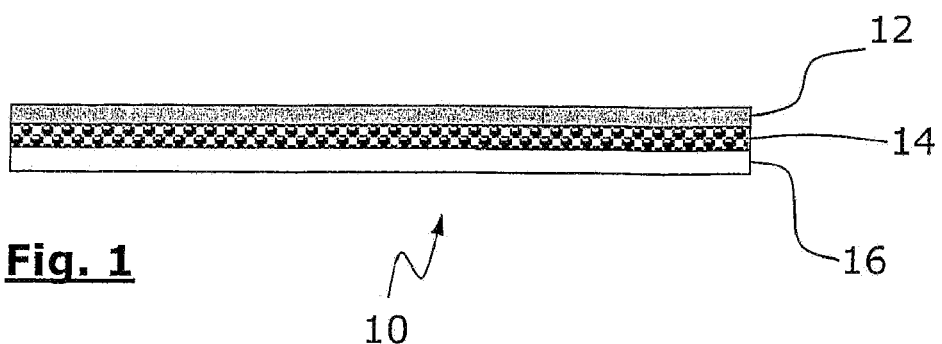
Fig. 1
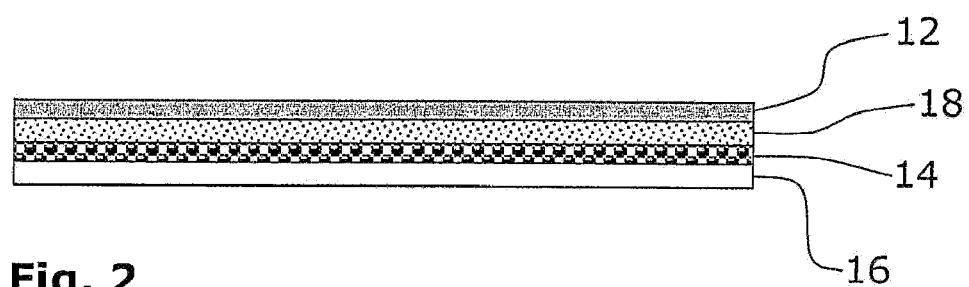
Fig. 2
Fig. 3
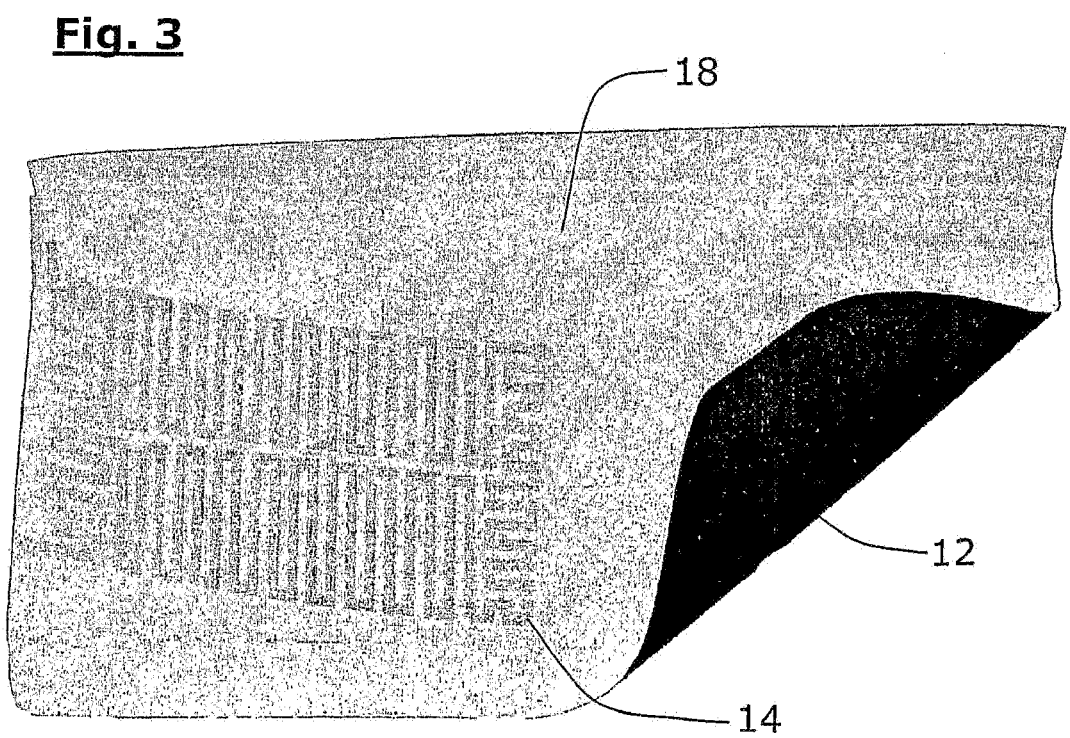

HEATER ELEMENT INCORPORATING FUNCTIONAL ELECTRICAL CIRCUIT

CROSS REFERENCE TO RELATED APPLICATION

This application is a divisional of U.S. Ser. No. 10/559,024, filed Apr. 13, 2006.

BACKGROUND OF THE INVENTION

1. Field of the Invention

The present invention relates to a garment or garments incorporating a functional electrical or electronic circuit. Preferably, the invention relates to the incorporation into a garment of a breathable, porous, flexible fabric circuit for use as a heater. The garment may include a thermally activated chemical delivery system. The circuit may be used as an electrical interconnect (electro-conductive) system with or without electronic devices, e.g. as a keypad or keyboard.

2. Related Art

A primary function of garments designed for outdoor sports and leisure activities such as mountaineering, hiking, potholing, motorcycling, etc., is thermal protection, particularly from cold weather conditions. Similarly, such thermal protection is important in many work-wear applications (e.g. seamen, workmen, delivery personnel, refrigeration plant operators, airport workers, etc.) where, potentially, staff may be exposed to cold conditions for prolonged periods. Conventionally, protection from the cold has been achieved by incorporating within garments low-convection fabric structures capable of entrapping still air to provide thermal insulation (e.g. waddings or battings). The thermal insulation achieved by such structures is principally a function of fabric thickness: the insulation increases with fabric thickness. Therefore, existing garments with high thermal insulation can be thick and bulky and may have limited conformability. This can restrict the mobility and comfort of the wearer in use, which is disadvantageous.

The designs of various active heating systems capable of evolving heat in response to an energy input are known. These systems involve incorporating materials into fibres or films, coatings and laminated structures and specify the use of (for example); phase change materials, metals and exothermic materials. The incorporation of electrical heating systems within garments has also been described in the prior art and include continuous metallised fabric (GB-A-2092868), woven carbonised filament (U.S. Pat. No. 6,172,344 and GB-A-2336514) and insulated conductive yarn (U.S. Pat. No. 6,501,055) heating elements.

SUMMARY OF THE INVENTION

The present inventor has realised that there is a need for a breathable flexible heater which is capable of being incorporated into a garment. Typically, such incorporation should not compromise the flexibility or conformability of the garment. Ideally, such a heater could be capable of forming part of the garment assembly rather than being "bolted-on", which is a cumbersome approach. Preferably, the heater system should also allow the garment to maintain its vapour management characteristics (e.g. breathability) and not interfere with other performance characteristics that govern the functionality of the garment in use (e.g. air permeability, wind and waterproofing). Preferably, the heating of the garment can be applied locally only to those areas of the garment that require heating. Preferably also, regulation of the heater element temperature is enabled.

Accordingly, in a first aspect, the present invention provides a flexible heater system for incorporation into a garment. Typically, the heater can be incorporated as a lining into the garment without complicating the design of the garment and without significantly interfering with other aspects of the garment's functionality.

Preferably, the heater system includes a porous metallised fabric heater element. The advantage of this is that the microclimate of the garment to which the heater system is to be applied will be substantially unaffected by the presence of the heater system when the heater system is not in operation. Of particular importance to the microclimate of a garment is the breathability of the garment, i.e. the ability for water vapour to pass from the wearer of the garment, through the garment to the outside surface of the garment.

Typically, the heater element is formed by photochemical etching of porous metallised fabric.

Details of the construction, manufacture and heating performance of a suitable flexible, porous etched metallised fabric heater are described in WO03/053101, the content of which is incorporated by reference in its entirety. WO03/053101 claims priority from UK Patent Application No. 0228999.9, filed 14 Dec. 2001.

Preferably, the porous etched metallised fabric heater element with an appropriate track pattern is encapsulated in or laminated between layers of a suitable continuous polymer to produce a waterproof, flexible heater element. The thickness of the heater element is preferably less than 1 mm. The heater element may be connected to a portable battery so as to be powered to deliver significant thermal energy to the wearer.

In a preferred embodiment, the heater element is formed into a laminate by applying a breathable face fabric to the heater element.

The width, length and shape of the etched track pattern can be selected from a wide range in order to optimise the heater element performance or to provide differential heating.

In use, the heater element may be controlled to regulate the rate of heating and/or the maximum heat output. Suitable temperature regulation can be achieved either manually by the wearer or via a suitable control device. Suitable control devices may incorporate a surface mounted thermistor. Alternatively, temperature regulation can be achieved by limiting the resistance of the heater itself.

Ensuring that the heater element is thin and flexible allows minimisation of stiffening or reduction in conformability of the garment. Garments containing the heater element may be deformed, bent and packed for storage. Garments containing the heater element may also be washed (e.g. machine washed or hand washed) without removing the heater element from the garment. Such heater elements are able to retain their electrical heating function after such treatments.

It is intended that the heater element can be incorporated into existing garments, e.g. by the garment manufacturer, without the need for major modifications to the construction and/or design of such existing garments.

Preferably, the heater element is incorporated into a laminated structure. The laminated structure may include, in addition to the heater element, an outer face fabric (e.g. a woven fabric of man-made fibres). The laminated structure may further include an inner lining fabric. The inner lining fabric may be a woven, knitted, nonwoven or mesh fabric.

Typically, lamination of the fabrics into the laminated structure is carried out using known processes. Preferably, thermoplastic adhesives in the form of meltblown webs, grids, mesh structures and/or films are used. Particle binders can also be applied by spraying or coating onto one or more of the surfaces to be laminated. The laminate may be produced by calendaring or pressing at an appropriate temperature or using any other known technique.

The laminated structure may include a breathable film or membrane that is substantially impervious to liquid water (e.g. rainwater) but which allows water vapour to pass through.

The heater element may be laminated to the required fabrics (e.g. the face fabric) using a thermoplastic web material. Such materials are typically fibrous and have a high degree of open porosity. Typical thermoplastic webs soften when heated (e.g. to around 130.degree. C.). Pressure may be applied to speed up the softening of the material. Typically, the thermoplastic web material is located between the heater element and the face fabric. The arrangement is then heated and pressed so that the thermoplastic web is softened and deformed so as to adhere the heater element to the face fabric to form a laminate. For example, an industrial ironing process may be used to laminate the heater element and face fabric in this way.

The heater element may be incorporated into a drop-liner for a garment.

The heater element may be incorporated in a detachable liner for a garment.

The present inventor has realised that the present invention may have a further advantage over known garments. It is preferred to incorporate functional chemicals into an laminate structure according to an embodiment of the invention or into a garment for use with the laminate structure, said functional chemicals being ones that are capable of being initiated by operation of the heater element.

Preferably, the invention provides heat-activatable agents for release due to heat generated by the heater element.

The chemicals (or agents) of interest include antimicrobials (for suppressing or killing microbiological activity, e.g. bacteria), insect repellants (for repelling insects such as mosquitoes etc.), fragrances and perfumes.

In a preferred approach, the chemicals (or agents) of interest are microencapsulated in microcapsules. Suitable microcapsules are those that melt at a particular initiation temperature. Alternative microcapsules are those that allow diffusion of the active chemicals through their walls to effect a slow release mechanism within the garment. By appropriate temperature control, the heater element in the garment may then be used to initiate the delivery of such active chemicals or agents.

It will be understood that by the encapsulation of various active chemicals and the use of microcapsules having different thermal characteristics, the timing of the delivery of each chemical can be controlled as required. Normally, the microencapsulated components will not form part of the heater element itself. Instead they will typically be contained within other layers of the laminate structure e.g. the inner fabric layer. The release of the chemicals is typically achieved using the heater, which is preferably adjacent to the layer containing the microencapsulated components. The breathability of the fabric heater assists the circulation of the released functional chemicals.

The operation of the heater element may be controlled in such a way so as to provide a time-varying heating profile to the garment.

Furthermore, the present inventor has realised that the tracks of the flexible metallised fabric can be used as electrical interconnects in a functional circuit to be incorporated in a garment. In this way, the invention can be used as an electrical interconnect between circuit components.

Accordingly, in another aspect, the present invention provides a breathable garment flexible electrical interconnect formed from porous metallised fabric, for use in a garment.

Preferred or optional features of the heater element are also preferred or optional features for the electrical interconnect, where appropriate.

In adapting the invention for this use, the heater element set out above need not be operated as a heater in use, i.e. the heat generated by the tracks of the metallised fabric need not be significant enough to provide significant heat to the garment. Thus, the present invention may provide a garment incorporating a functional electrical circuit. The circuit may include active and/or passive components, e.g. LEDs. These may be fixed to the tracks of the circuit using solder, conductive adhesive or other known conductive attachment techniques. Materials having desired electronic properties may be applied to the metallised fabric in order to create discrete electronic components. For example, resistive or dielectric materials may be applied in this way, giving rise to a textile circuit having useful functional circuit properties. For example, such a textile circuit may be built into a garment to provide a keypad, e.g. for a mobile phone, or a keyboard or other data entry or control device.

In a still further aspect, the invention provides a fabric electronic device for data entry or control, incorporating an electrical interconnect as set out above.

Preferably, the device is configurable between a storage configuration and a use configuration by unrolling.

In any of the aspects of the invention set out above, the flexible metallised fabric may be shaped so as to provide terminals for electrical connection of tracks formed on the fabric at an elongate flexible tail portion of the fabric. In this way, the functional part of the shape (e.g. the heater element part or the complex circuitry tracks) may be connected to a suitable power supply via the terminals at the tail portion. This avoids the need for conventional wires to be trailed through the garment from the power supply to the fabric.

BRIEF DESCRIPTION OF THE DRAWINGS

Preferred embodiments of the invention will now be described, by way of example, with reference to the accompanying drawings, in which:

FIG. 1 shows a schematic cross-sectional view of a laminated fabric according to an embodiment of the invention.

FIG. 2 shows a schematic cross-sectional view of a laminated fabric according to another embodiment of the invention.

FIG. 3 shows a schematic plan view of a laminated fabric according to an embodiment of the invention but without an inner fabric layer.

DETAILED DESCRIPTION OF THE PREFERRED EMBODIMENTS

Figure 4:
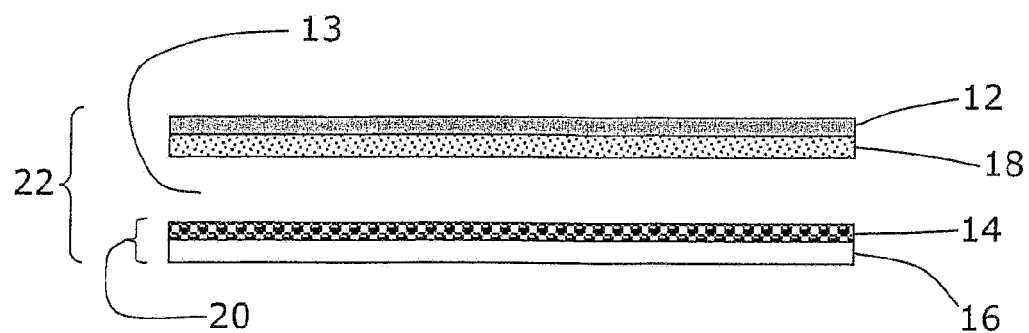
FIG. 4 shows a schematic cross-sectional view of a laminated fabric according to another embodiment of the invention.

FIG. 1 shows a laminated fabric structure 10 having three layers. Heater element layer 14 is sandwiched between face fabric layer 12 and inner fabric layer 16.

FIG. 2 shows an alternative laminated fabric structure having four layers. Heater element layer 14 is sandwiched between breathable film or coating 18 and inner fabric layer 16. Face fabric layer 12 is disposed on breathable film 18.

FIG. 3 shows a schematic plan view of a laminated fabric according to an embodiment of the invention but without an inner fabric layer 16. One corner of the limited structure is shown turned over to expose the face fabric layer 12. Breathable layer 18 is disposed on the back surface of face fabric layer 12. Heater element layer 14 is located on the breathable layer. Inner fabric layer 16 is not shown for the sake of clarity.

A suitable power supply (not shown) for the heater is supplied by Mpower Batteries Limited, consisting of 2.times.3.6 V lithium ion batteries. Suitable control circuitry is also available from the same source. See also the control circuitry disclosed in WO 03/039417.

The conductive track pattern of the heater element is shown in FIG. 3. The way in which a metallised fabric may be used to create a suitable heater element will now be described.

The heater element is formed by taking a nickel coated polyester woven fabric and cutting it to the desired shape for the garment of interest. A suitable material is the commercially available metallised fabric Metalester (Registered Trade Mark), a woven electroless nickel plated polyester mesh. Such fabrics are available with a variety of thread thicknesses, thread spacings, type of weave and weight of nickel. Threads may typically have a diameter within the range 24 to 600 micrometers (microns), a thread count of between 4 and 737 per cm, and a metal coating of varying weight per square metre.

Suitable fabrics may be coated with a continuous layer of metal after manufacture, for example by sputtering, by chemical reduction or by electro-deposition, which results in total encapsulation of all the threads of the mesh in metal. In an alternative mesh, the individual warp and weft threads may be metallised prior to fabric production, for example by sputtering, by chemical reduction or by electro-deposition.

After selecting the desired metallised fabric and cutting it to the required shape, the desired track pattern is then photochemically etched from the fabric. This is done by first designing and generating a suitable phototool, in a way well known to the skilled person. Next, the fabric is mounted onto a hinged frame of brown styrene board, so that the otherwise flimsy fabric can be more readily handled. The fabric is then cleaned with a commercial surface cleaning agent to assist in the adhesion of the photoresist. Then, the photoresist is applied, typically by dip-coating the fabric into a liquid photoresist to ensure application of the photoresist to all parts of the fabric by immersion.

Next, the fabric is exposed to a suitable image pattern of ultraviolet light from the phototool. This image is developed. The unrequired metal is then progressively etched away. Then, the photoresist is removed to leave the required metallic track shape for the heater element. These steps will be clear to the skilled person. The metallic track is indicated by reference numeral 14 in FIG. 3.

In the embodiment of the invention shown in FIG. 1, the flexible heater element is combined into a laminated structure 10 by thermal adhesion. The laminate consists of the outer face fabric 12, which is typically a woven fabric composed of man-made fibres, the heater element 14 and the inner lining fabric 16, which ordinarily may be a woven, knitted, nonwoven or mesh fabric.

Lamination is achieved using conventional processes. Preferably, thermoplastic adhesives in the form of meltblown webs, grids, mesh structures and films are used. Particle binders can also be applied by spraying or coating on to one or more of the surfaces to be laminated. The laminate is produced by calendaring or pressing at an appropriate temperature or using any other known technique.

A suitable thermoplastic web material is the melt-spun interlining material Vilene (registered trade mark) U25 supplied by Freudenberg Nonwovens Interlining Division (part of Freudenberg Vliesstoffe KG). The U25 grade is made from 100% polyamide and has a random web structure and a weight of 25 grams per square metre. The material softens and fuses when heat is applied at about 130.degree. C. for about 10 seconds with a pressure of 15-30 N/cm.sup.2. The web has a high degree of open porosity and so allows the lamination between the face fabric and the heater element to give rise to a breathable structure.

In some protective garments a breathable film/membrane or coating is incorporated to prevent the penetration of liquid water and wind. At the same time, this film is intended to allow the passage of water vapour from the wearer to the outside environment to improve comfort. Commonly, this breathable film is applied to the back of the face fabric as shown in FIG. 2 or is laminated between the face fabric and the inner lining. In such garments, the heater element is incorporated between the breathable membrane/coating and the inner lining.

FIG. 4 shows a laminated structure 22 according to another embodiment of the invention. Similar features to those shown in the other drawings are given the same reference numerals for the sake of clarity. The structure of FIG. 4 is intended for use as a drop-liner within a garment. The heater element 14 is laminated to the inner fabric layer 16. An air gap 13 is provided between the heatable inner lining 20 and the outer face fabric 12 and breathable membrane 18 by only loosely attaching the inner lining 20 (i.e. not over its entire surface) to the outer face fabric and breathable membrane.

It is also contemplated that the outer face fabric 12 need not have a breathable membrane.

FIGS. 1, 2, 3 and 4 show garment systems where the linings may not be designed to be removable and the heater element is fully integrated within the lining fabrics. In some garments it is advantageous to have a removable or detachable lining to allow them to be interchanged with others depending on weather conditions or removed for washing for example. Such inner linings may often be fixed in to the garment using a zip, mounted around the circumference of the inner lining.

Figure 5:
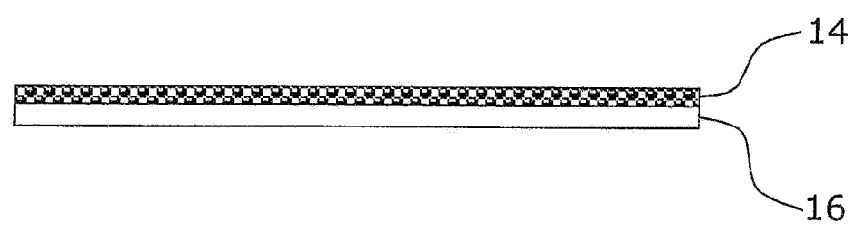
FIG. 5 a schematic cross-sectional view of a laminated fabric according to another embodiment of the invention.

In another embodiment, the heater element is laminated to the inside of the inner lining, which may be a woven, knitted, nonwoven or mesh structure, as shown in FIG. 5. This laminated structure is intended to be removable using any commonly used fixation system such as a zip fastener or a hook-and-loop system. The inner lining fabric may be a fleece or pile fabric depending on the design and intended use of the garment.

It will be understood that whilst specific examples are provided, other laminated, drop and mid-liner combinations are possible in garments and these are within the spirit and scope of the present invention.

In a further embodiment, functional chemicals are incorporated into the laminated structure or the garment. The functional chemicals can be initiated by the heat generated by the heater element. Such chemicals include antimicrobials (to suppress or kill microbiological activity), insect repellants (to repel mosquitoes etc.) fragrances and perfumes. In a preferred approach such chemicals are microencapsulated in microcapsules, which melt at a particular initiation temperature or others, which allow diffusion of the active chemicals through their walls to effect a slow release mechanism within the garment. By appropriate temperature control, the heater element in the garment is then used to initiate the delivery of such active chemicals.

It will be understood that by the encapsulation of various active chemicals and the use of microcapsules having different thermal characteristics, the timing of the delivery of each chemical can be controlled as required. Normally, the microencapsulated components will not form part of the heater element itself rather they will be contained within other layers of the garment e.g. the face fabric layer. The release of the chemicals is however achieved using the heater, which is preferably situated next to the layer which incorporates the microencapsulated components.

For the specific example of a microencapsulated insect repellent, the microcapsules of US-A-20030124167 are incorporated into the face fabric layer.

Suitable materials for encapsulating suitable agents include lipids such as wax, paraffin, tristearin, stearic acid, monoglycerides, diglycerides, beeswax, oils, fats and hardened oils.

Suitable perfumes and fragrances are known. These may be encapsulated in wax, for example.

Microencapsulated fragrances are available from Celessence International, of Hatch End, Pinner, Middlesex, HA5 4AB, UK.

In another embodiment, the invention is extended to create a garment which incorporates an electro-conductive circuit. Active and passive components are mounted to the fabric circuit track using solder or a conductive adhesive or similar attachment systems. In addition, electronic materials e.g. resistive or dielectric materials can be applied to the fabric circuit to create discrete components thus allowing a complete functional electronic circuit board to be made. The invention utilises a porous, etched fabric circuit as described above. The resulting electro-conductive textile circuit can be incorporated in to a garment in a similar manner as described in relation to FIGS. 1-5 to improve functionality and to enable the control of associated equipment for example, mobile phone keypads, military applications etc.

Figure 6:
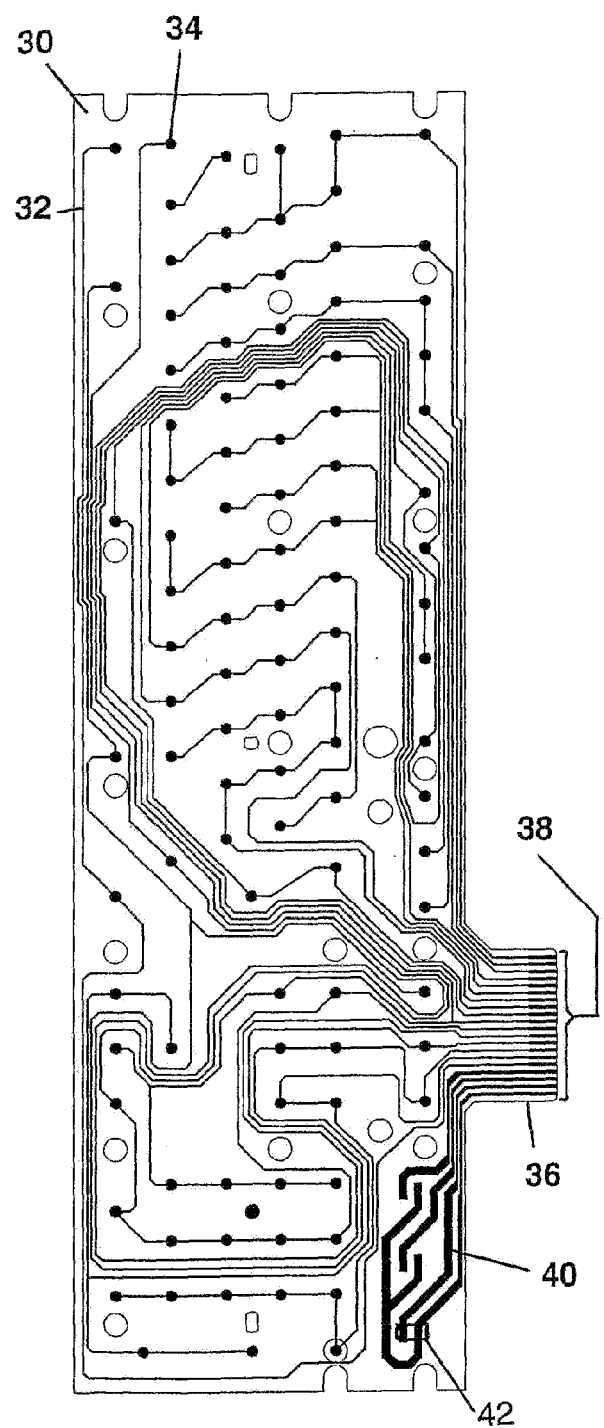
FIG. 6 shows a schematic layout of tracks for a first layer for a fabric keypad according to an embodiment of the invention.

FIG. 6 shows a schematic layout of conductive tracks for a first layer for a fabric keypad according to an embodiment of the invention. The metallised fabric layer 30 is photochemically etched to produce the track layout shown and then cut to the required shape. Tracks 32 follow a known layout between contact pads 34. Tracks 32 lead to terminals 38 on flexible tail portion 36. The tail portion 38 shown in this drawing is short, but it will be clear to the skilled person that the formation of a significantly longer tail portion is easily accomplished in the light of the present disclosure.

Thicker tracks 40 are also formed. These provide electrical connections for LEDs (not shown) to be connected between adjacent tracks, e.g. at location 42.

Figure 7:
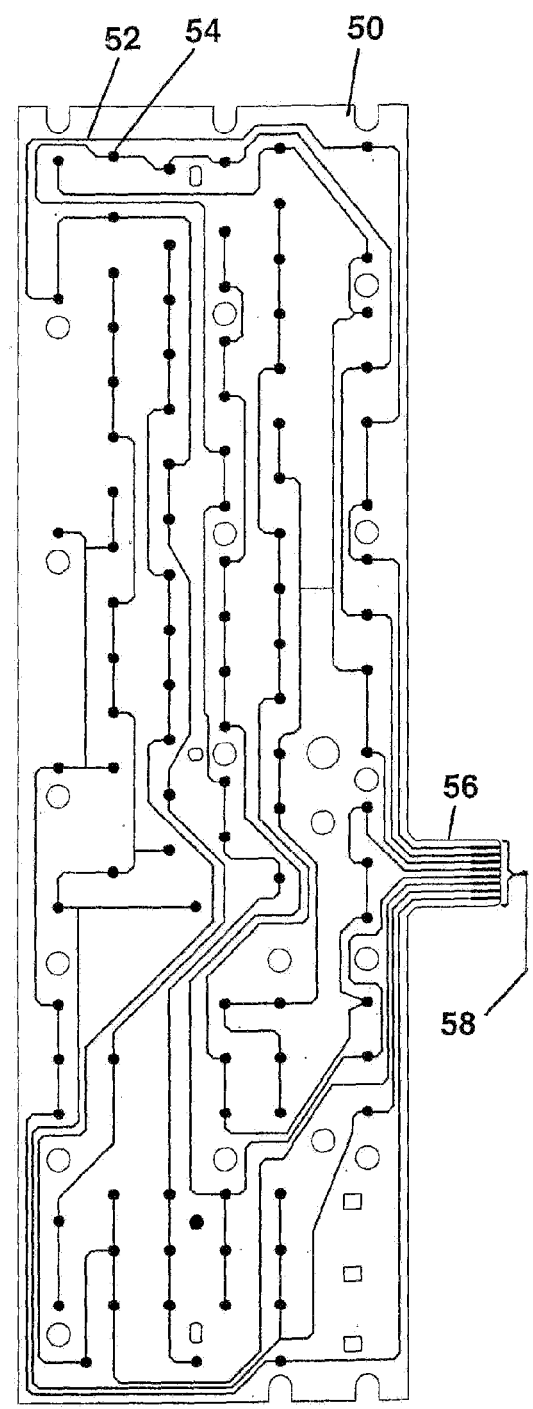
FIG. 7 shows a schematic layout of tracks for a second layer for a fabric keypad, to be used in conjunction with the layer of FIG. 6.

FIG. 7 shows a schematic layout of tracks for a second layer for a fabric keypad, to be used in conjunction with the layer of FIG. 6. The metallised fabric layer 50 is photochemically etched to produce the track layout shown and then cut to shape. Tracks 52 follow a known layout between contact pads 54. Tracks 52 lead to terminals 58 on flexible tail portion 56.

When assembled into the fabric keypad device, the first layer 30 is laid over the second layer 50 with a spacer layer (not shown) located between them. As will be seen from FIGS. 6 and 7, the overlaying of the layers brings corresponding contact pads into register with each other. The second layer is covered by another fabric layer having key designations printed on it, e.g. by thermostatic printing (registered trade mark). Pressure applied to a particular key by a user's finger pushes contact pad 54 into electrical contact with contact pad 34 through a corresponding hole through the spacer layer, completing a circuit. This circuit completion is recognised by suitable known control means, and the function corresponding to that key is carried out in a known way. For example, in the case of a TV remote control, a suitable signal is sent from the TV remote control corresponding to the key pressed. Alternatively, in the case of a mobile phone keypad, a number signal is sent to a display device. Alternatively, in the case of a keyboard, a signal corresponding to the key depressed is sent to a computer or other data manipulation device.

Of course, the flexible electrical interconnect need not be used in a garment. It may be produced as an independent device, e.g. as a roll-up keyboard or the like. Given the disclosure of the flexible device for incorporation in a garment, the skilled person will be able to produce such an independent device.

The above embodiments have been described by way of example. Modifications of these embodiments, further embodiments and modifications thereof will be apparent to the skilled person and as such are within the scope of the invention.

What is claimed is:

1. A heater element that is easily applied to an object to be heated, comprising:
   a heat generating layer having a first side and a second side; the heat generating layer including a metallised substrate of porous fabric having a plurality of components each encapsulated in metal wherein the metal on the metallised substrate of fabric is photochemically etched by selectively etching out metal encapsulated about the plurality of components of substrate of porous metallised fabric; and
   means for adhering the heat generating layer to a surface of an object to be heated; the means for adhering residing on the first side of the heat generating layer.

2. The heater element of claim 1, wherein the means for adhering is selected from the group consisting of adhesive, melt spun material, thermoplastic adhesive, hook and loop fastener material and zipper.

3. The heater element of claim 1, further comprising:
   a first protective layer on the first side of the heat generating layer.

4. The heater element of claim 3, wherein the first protective layer is secured to the first side of the heat generating layer by an adhesive.

5. The heater element of claim 1, further comprising:
   a second protective layer on the second side of the heat generating layer.

6. The heater element of claim 5, wherein the second protective layer is secured to the second side of the heat generating layer by an adhesive.

7. The heater element of claim 1, wherein the heat generating layer is made of a material selected from the group consisting of: woven, non-woven, knitted, laminated composite, pressed felt and braided materials.

8. The heater element of claim 1, further comprising:
a power supply electrically connected to the metallised fabric for providing electricity thereto to cause the heat generating layer to generate heat.

9. The heater element of claim 8, further comprising:
termination pads electrically connected to the metallised fabric and the power supply.

10. The heater element of claim 1, wherein the heater element is substantially impervious to liquid water but allows water vapor to pass therethrough.

11. The heater element of claim 1, wherein the object to be heated is a garment.

12. The heater element of claim 1, further comprising:
a thermal protection device to allow temperature control of the heater element.

13. The heater element of claim 1, wherein the metallised fabric is coated with a continuous layer of metal.

14. The heater element of claim 1, wherein the components of the substrate of porous metallised fabric are woven from polyester threads and the metal is nickel.

15. The heater element of claim 1, wherein the metallised substrate of porous fabric is laminated between layers of a polymer to produce a waterproof, flexible heater element.

16. The heater element of claim 1, further comprising:
heat activatable agents for release due to heat generated by the heater element.

17. The heater element of claim 1, wherein the components of the substrate of porous metallised fabric are individual yarns, the individual yarns being encapsulated in metal prior to the manufacture of the substrate of porous metallised fabric.

18. The heater element of claim 1, wherein the components of the substrate of porous metallised fabric are individual fibres, the individual fibres being encapsulated in metal prior to the manufacture of the substrate of porous metallised fabric.

19. The heater element of claim 1 wherein the components of the substrate of porous metallised fabric are individual yarns, the individual yarns being encapsulated in metal after manufacture of a substrate of a porous fabric to form the substrate of porous metallised fabric.

20. The heater element of claim 1 wherein the components of the substrate of porous metallised fabric are individual fibres, the individual fibres being encapsulated in metal after manufacture of a substrate of a porous fabric to form the substrate of porous metallised fabric.

* * * * *